(12) United States Patent
Aufricht

(10) Patent No.: US 9,931,369 B2
(45) Date of Patent: Apr. 3, 2018

(54) CARBOHYDRATE-BASED PERITONEAL DIALYSIS FLUID COMPRISING GLUTAMINE RESIDUE

(71) Applicant: Zytoprotec GmbH, Vienna (AT)

(72) Inventor: Christoph Aufricht, Klosterneuburg (AT)

(73) Assignee: ZYTOPROTEC GMBH, Vienna (AT)

( * ) Notice: Subject to any disclaimer, the term of this patent is extended or adjusted under 35 U.S.C. 154(b) by 0 days.

(21) Appl. No.: 14/081,835

(22) Filed: Nov. 15, 2013

(65) Prior Publication Data

US 2014/0142051 A1 May 22, 2014

Related U.S. Application Data

(63) Continuation of application No. 12/529,537, filed as application No. PCT/AT2008/000072 on Mar. 3, 2008, now abandoned.

(30) Foreign Application Priority Data

Mar. 2, 2007 (AT) .................................. A 340/2007

(51) Int. Cl.

| | |
|---|---|
| A61K 38/05 | (2006.01) |
| A61K 31/198 | (2006.01) |
| A61K 38/06 | (2006.01) |
| A61K 38/07 | (2006.01) |
| A61K 38/08 | (2006.01) |
| A61M 1/28 | (2006.01) |

(52) U.S. Cl.
CPC ............ *A61K 38/05* (2013.01); *A61K 31/198* (2013.01); *A61K 38/06* (2013.01); *A61K 38/07* (2013.01); *A61K 38/08* (2013.01); *A61M 1/287* (2013.01)

(58) Field of Classification Search
None
See application file for complete search history.

(56) References Cited

U.S. PATENT DOCUMENTS

| | | | |
|---|---|---|---|
| 4,796,683 A | 1/1989 | Kawabata et al. | |
| 5,561,111 A * | 10/1996 | Guerrant et al. | 514/5.5 |
| 5,589,197 A * | 12/1996 | Shockley et al. | 424/663 |
| 6,077,836 A | 6/2000 | Milner | |
| 6,156,797 A * | 12/2000 | Kubo | A61K 33/14 424/663 |
| 6,656,719 B1 * | 12/2003 | Gould et al. | 435/235.1 |
| 6,979,560 B1 | 12/2005 | Livshits et al. | |
| 7,211,662 B2 | 5/2007 | Backer et al. | |
| 2003/0232093 A1 | 12/2003 | Faict et al. | |
| 2005/0074485 A1 | 4/2005 | Lipton | |
| 2005/0226856 A1 * | 10/2005 | Ahlfors | 424/93.7 |

FOREIGN PATENT DOCUMENTS

| | | |
|---|---|---|
| EP | 0207676 A2 | 1/1987 |
| EP | 0970699 A2 | 1/2000 |
| EP | 1166787 A2 | 1/2002 |
| EP | 1369432 A2 | 12/2003 |
| EP | 1563858 A1 | 8/2005 |
| JP | 2003-019198 A | 1/2003 |
| KR | 2001-0008659 A | 2/2001 |
| WO | WO 82/03773 A1 | 11/1982 |
| WO | WO 94/14468 A1 | 7/1994 |
| WO | WO 95/19778 A1 | 7/1994 |
| WO | WO 99/01144 A1 | 1/1999 |
| WO | WO 01/02004 A1 | 1/2001 |
| WO | WO 2007/016791 A1 | 2/2007 |

OTHER PUBLICATIONS

Goeters et al ('Parenteral L-alanyl-L-glutamine improves 6-month outcome in critically ill patients' Crit Care Med 2002 v30(9) pp. 2032-2037).*
Chemical book (retrieved from http://www.chemicalbook.com/ChemicalProductProperty_EN_CB5166004.htm on Feb. 13, 2015, 2 pages).*
Fard et al ('Circulating obestatin level in diabetic and obese rats' Tanta Medical Journal 2014 v41(1) pp. 1-5).*
Furst P. ('New developments in glutamine delivery' The Journal of Nutrition v131(9) Sep. 1 2001 pp. 2562S-2568S).*
Gjessing, J., "Addition of aminoacids to peritoneal-dialysis fluid", Lancet, vol. 2, No. 7572, Oct. 12, 1968, pp. 812.
Hiscock et al., "Exercise-induced immunodepression-plasma glutamine is not the link", J Appl Physiol, vol. 93, Sep. 2002, pp. 813-822.
Schambye, H.T., "Effect of different buffers on the biocompatibility of CAPD solutions", Peritoneal Dialysis International, Pergamon Press, New York, NY, US, vol. 16, No. Suppl. 1, Jan. 1, 1996, pp. S130-S136.

* cited by examiner

*Primary Examiner* — Karlheinz R. Skowronek
*Assistant Examiner* — Ronald T Niebauer
(74) *Attorney, Agent, or Firm* — Birch, Stewart, Kolasch & Birch, LLP

(57) ABSTRACT

The present invention relates to a carbohydrate-based peritoneal dialysis fluid, containing a compound selected from the group consisting of glutamine, preferably L-glutamine; a dipeptide capable of releasing glutamine, L-glutamine in free form, preferably selected from the group consisting of glutaminyl-glycine, glycinyl-glutamine, glutaminyl-alanine, alanyl-glutamine; an oligopeptide consisting of two to seven glutamine, preferably L-glutamine residues; and mixtures thereof. The peritoneal dialysis fluids of the present invention are useful for inhibition of technical failure in a person undergoing peritoneal dialysis treatment.

11 Claims, 3 Drawing Sheets

CARBOHYDRATE-BASED PERITONEAL DIALYSIS FLUID COMPRISING GLUTAMINE RESIDUE

This application is a Continuation of U.S. patent application Ser. No. 12/529,537 filed on Sep. 1, 2009, which is the National Phase of PCT International Application No. PCT/AT2008/000072 filed on Mar. 3, 2008, which claims priority under 35 U.S.C. 119(a) to Austrian Patent Application No. A 340/2007 filed on Mar. 2, 2007, all of which are hereby expressly incorporated by reference into the present application.

The present invention relates to a peritoneal dialysis fluid (in the following also referred to as "PDF").

Peritoneal dialysis fluids remove solutes and water from the uremic patient. Several clinical and experimental observations have shown that PDF is cytotoxic, associated with a risk of technical failure of up to 30% with long term peritoneal dialysis (PD) treatment (6). Therefore, prolonged PD treatment frequently results in severe chronic damage to the integrity of the peritoneal membrane. Bio-incompatibility of PDF and peritoneal inflammation are regarded as the major culprits. PDF exposure impairs peritoneal cell metabolism, reduces proliferation and increases cell death, as well as disrupts cytoskeletal organization and cell signaling, including the regulation of differentiation and inflammation. This results in aberrant healing processes, epithelial-mesenchymal transdifferentiation, neoangiogenesis, fibrosis and chronic scarring of the peritoneal membrane (7). Analysis of sequential peritoneal biopsy specimens from patients undergoing PD revealed deleterious structural alterations. In severe cases, mesothelial cells have detached, the peritoneum is denuded and covered with a thick amorphous layer of connective tissue. These morphological changes result in severe disruption of the barrier function of the peritoneum as a semi-permeable dialysis membrane. Up to a third of adult patients on PD will suffer from technical failure during the course of the treatment because of peritoneal membrane failure (6).

Current research therefore aims to increase biocompatibility of PDF and thereby reduce mesothelial cell damage during PD. New and improved formulations have indeed shown to be less toxic in several in-vitro and in-vivo, experimental and clinical studies (7,10). Addition of the antioxidant/scavenger Carnosine (a β-alanyl-L-histidine dipeptide), or Glutathion (gamma-glutamyl-L-cysteinyl-glycine) and related compounds (such as the cysteine pro-drug L-2-oxothiazolidine-4-carboxylate) were shown to have a positive influence on PDF biocompatibility and to passively reduce the deleterious impact of glucose degradation products in PD (20-22).

However, the main working principle of PDF is removal of solutes and water from the uremic patient due to its hypertonicity. PDF will therefore likely never represent a physiologically inert or completely biocompatible fluid and repeated filling and drainage to and from the abdominal cavity will always retain some cytotoxicity.

The above-mentioned disadvantages especially apply to carbohydrate-based PDF. Under "carbohydrate-based" PDF the skilled artisan understands a peritoneal dialysis fluid based on glucose or glucose-oligomers and glucose-polymers as the osmotic agent. PDF's based on glucose are preferably used in the present invention and may typically contain from 10 to 45 g/l glucose (cf. EP 1 166 787). Further examples of carbohydrate-based PDF's are disclosed in WO 82/03773 A1, U.S. Pat. No. 4,976,683 A, WO 01/02004 A1, US 2003/0232093 A1, EP 1 369,432 A2, KR 2001/008659, WO 94/14468 A1, WO 99/01144 A1, U.S. Pat. No. 6,077,836 A, WO 95/19778 A1, US 2005/0074485 A1, EP 0 207 676 A2 and WO 93/14796.

Recently, it was demonstrated that cytotoxicity of, especially, glucose-based PDF not only results in cellular injury, but also activates an endogenous machinery found in every cell, the heat-shock proteins (HSP) in mesothelial cells in in-vitro, ex-vivo and in-vivo models of PD (1-4,16). Whereas earlier studies focused on HSP upregulation as a marker of PDF biocompatibility, more recent data made evident that HSP protect mesothelial cells during experimental PD (3,5,9).

Overexpression of HSP resulted in survival of an usually lethal PDF exposure in the in-vitro model of PD and prevented mesothelial cells from detachment from their peritoneal lining in the in-vivo model of PD (5,9).

However, none of the used protocols to induce overexpression of HSP—such as hyperthermia or transient transfection—are attractive approaches in the clinical setting of PD.

BRIEF SUMMARY OF THE INVENTION

It is an object of the present invention to provide a carbohydrate-based peritoneal dialysis fluid which has less cytotoxicity than previously known products. Especially, it is an object of the present invention to provide a carbohydrate-based peritoneal dialysis fluid which inhibits technical failure in a patient undergoing a PD-treatment by actively optimizing cellular responses to pathophysiological stress upon PDF exposure.

DETAILED DESCRIPTION

Figure 1:
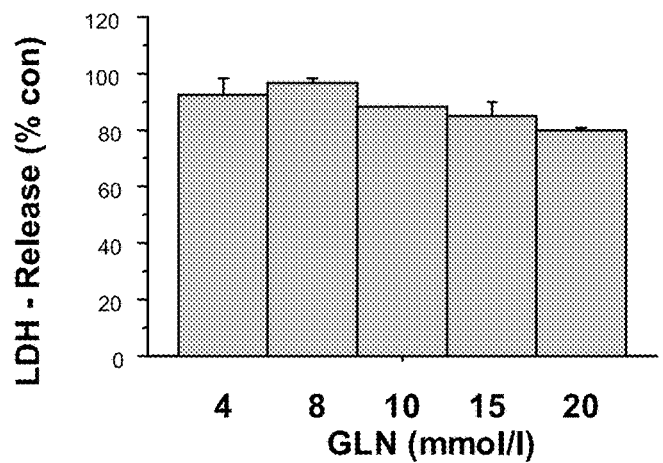
FIG. 1: The viability effects of L-glutamine exposure on cultured human mesothelial cells.

The term "technical failure" is well-known to the skilled artisan and means the need to terminate peritoneal dialysis, and to switch to alternate renal replacement therapies such as hemodialysis (6). Especially inhibiting technical failure includes steps to prevent peritoneal membrane failure and to attenuate barrier dysfunction and to prevent mesothelial cell detachment.

This object is solved by a carbohydrate-based peritoneal dialysis fluid containing a compound selected from the group consisting of
- glutamine, preferably L-glutamine,
- a dipeptide capable of releasing glutamine, preferably L-glutamine, in free form, preferably selected from the group consisting of glutaminyl-glycine, glycinyl-glutamine, glutaminyl-alanine and alanyl-glutamine
- an oligopeptide consisting of two to seven glutamine, preferably L-glutamine residues and mixtures thereof.

Furthermore, this object is solved by a compound selected from the group consisting of
- glutamine, preferably L-glutamine,
- a dipeptide capable of releasing glutamine, L-glutamine in free form, preferably selected from the group consisting of glutaminyl-glycine, glycinyl-glutamine, glutaminyl-alanine and alanyl-glutamine
- an oligopeptide consisting of two to seven glutamine, preferably L-glutamine residues and
- mixtures thereof for the specific use of inhibiting technical failure in a peritoneal dialysis treatment with a carbohydrate-based peritoneal dialysis fluid.

The object of the present invention is also solved by a carbohydrate-based peritoneal dialysis fluid comprising a compound selected from the group consisting of
- glutamine, preferably L-glutamine,
- a dipeptide capable of releasing glutamine, preferably L-glutamine, in free form, preferably selected from the group consisting of glutaminyl-glycine, glycinyl-glutamine, glutaminyl-alanine and alanyl-glutamine
- an oligopeptide consisting of two to seven glutamine, preferably L-glutamine residues and
- mixtures thereof for the specific use of inhibiting technical failure.

It has surprisingly been found that glutamine induces HSP-expression in mesothelial cells. Moreover, it has been found that a carbohydrate-based dialysis fluid containing glutamine, or a dipeptide capable of releasing glutamine in free form, such as glutaminyl-alanine and alanyl-glutamine, has lower cytotoxicity than previously known products. The use of glutamine containing dipeptides such as glutaminyl-glycine and glycinyl-glutamine as precursors of glutamine is also advantageous.

Glutamine is non-toxic and has been previously reported to mediate cytoprotection by increasing HSP expression (14,18). In-vitro, pharmacologic doses of glutamine resulted in enhanced DNA binding of HSF-1 to its promoter, similar as described for indomethacine and other NSAIDs (11,12). Alternately, glutamine supplementation has shown to result in stabilization of HSP-72 mRNA under stressful conditions, thereby increasing HSP expression (8). However, the use of glutamine to enhance HSP-expression in mesothelial cells when exposed to PDF has not yet been proposed.

According to the present invention, glutamine may be used in its monomeric form and/or in the form of a dipeptide capable of releasing glutamine in free form. It is known that the administration of amino acids to mammals is better tolerated if they are administered in the form of a di- or tripeptide. Especially, glutamine is poorly soluble in aqueous solutions and is a relatively unstable amino acid and is therefore preferably used in the clinical setting as a dipeptide consisting of glutamine and another amino acid, preferably alanine and glycine (23). Dipeptides containing L-glutamine as a component are, e.g., disclosed in U.S. Pat. No. 5,189, 016.

Said dipeptide is preferably selected from the group consisting of alanyl-glutamine, glutaminyl-alanine, glutaminyl-glycine and glycinyl-glutamine.

In a preferred embodiment, the PDF according to the present invention contains said compound in an amount sufficient to enhance expression of Heat-Shock-Protein (HSP) in mesothelial cells.

The concentration of said compound, especially L-glutamine, in the fluid may range from 0.3 mM to 300 mM, preferably from 2 mM to 25 mM.

The peritoneal dialysis fluid according the present invention may be produced by a process which comprises the step of admixing the compound (i.e. glutamine in monomeric form or as a component of an oligopeptide as defined above) to a carbohydrate-based peritoneal dialysis fluid. The carbohydrate-based peritoneal dialysis fluid used for making the PDF according to the invention may be a standard product as currently commercially available.

Preferably, the compound is admixed to the carbohydrate-based peritoneal dialysis fluid in an amount sufficient to enhance expression of Heat-Shock-Protein (HSP) in mesothelial cells.

The present invention, furthermore, relates to the use of compound selected from the group consisting of
- glutamine, preferably L-glutamine,
- a dipeptide capable of releasing glutamine, preferably L-glutamine, in free form, preferably selected from the group consisting of glutaminyl-glycine, glycinyl-glutamine, glutaminyl-alanine and alanyl-glutamine
- an oligopeptide consisting of two to seven glutamine, preferably L-glutamine residues and
- mixtures thereof for the preparation of a carbohydrate-based peritoneal dialysis fluid for inhibiting technical failure.

For all embodiments, the PDF employed is preferably based on glucose.

The present invention is explained in more detail in the following on the basis of examples and figures exemplifying preferred embodiments of the invention.

Figure 2:
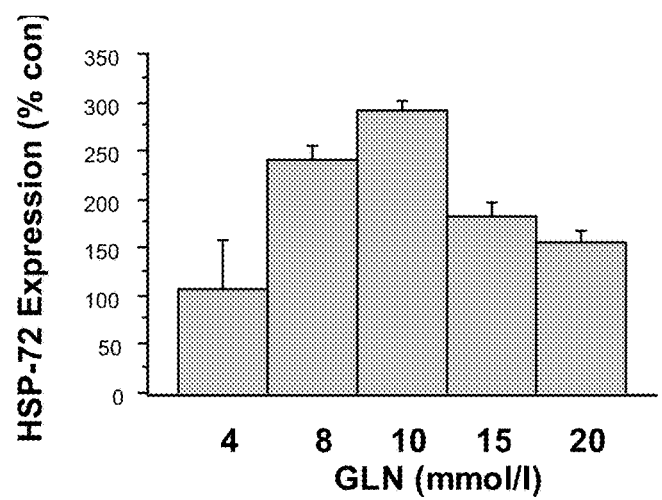
FIG. 2: HSP-72 expression in human mesothelial cells after exposure to increasing doses of glutamine.

In this regard, FIGS. 1 and 2 show the effects of L-glutamine exposure on cultured human mesothelial cells. Viability was assessed by LDH release (FIG. 1) and HSP-72 expression (FIG. 2) after exposure to increasing doses of glutamine (GLN) under control conditions. Addition of L-glutamine up to 20 mM resulted in unchanged viability. HSP-72 expression was enhanced at 8 and 10 mM glutamine concentration. Data are representative for 3 independent experiments.

Figure 3:
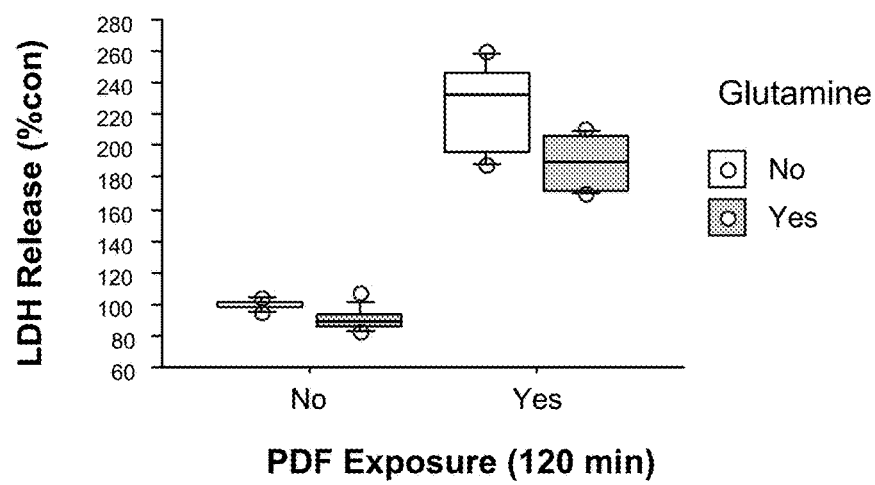
FIG. 3: LDH release by cultured human mesothelial cells after PDF-exposure.
Figure 4:
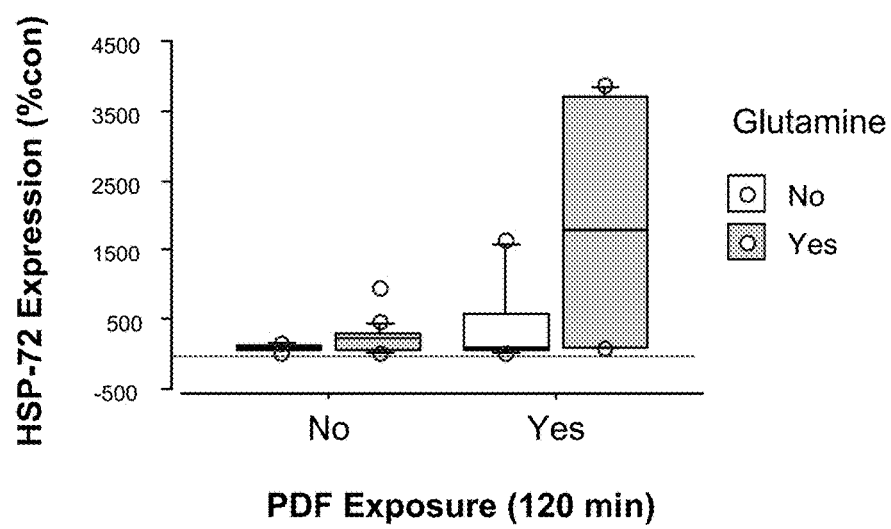
FIG. 4: HSP-72 expression after exposure to PDF with or without added glutamine.

FIGS. 3 and 4 show the effect of L-glutamine during PDF-exposure on cultured human mesothelial cells. Viability was assessed by LDH release (FIG. 3) and HSP-72 expression FIG. 4) after exposure to PDF with or without added glutamine (GLN) for 120 min. Data are shown as box (25th and 75th), whiskers (10th and 90th percentile) and median plot. Addition of L-glutamine resulted in significantly preserved viability and increased HSP-72 expression. Data are obtained from 6 experiments, the detailed statistics are given in the results section.

Figure 5:
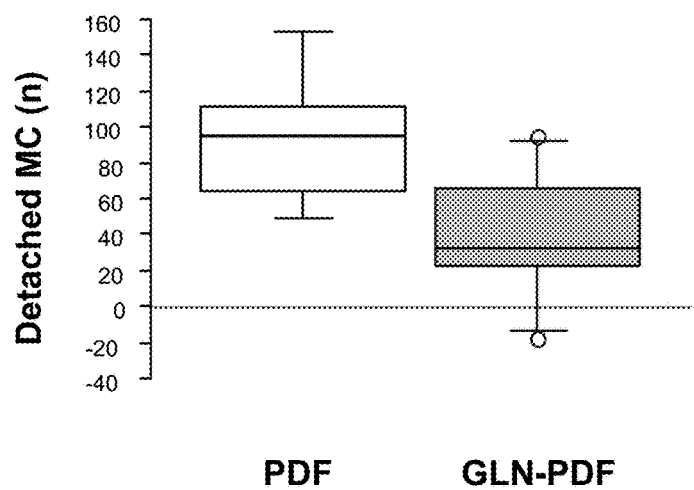
FIG. 5: Effect of pharmacologic manipulation of HSP-72 expression on mesothelial cell detachment.
Figure 6:
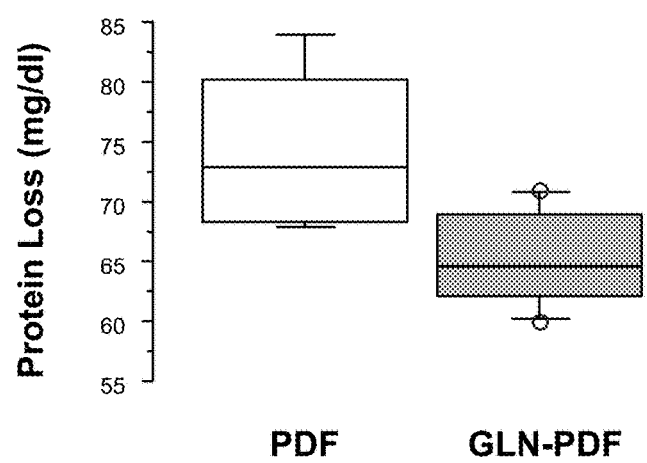
FIG. 6: Effect of pharmacologic manipulation of HSP-72 expression on peritoneal protein loss in the rat model of peritoneal dialysis.

FIGS. 5 and 6 show the effects of pharmacologic manipulation of HSP-72 expression on mesothelial cell detachment and peritoneal protein loss in the rat model of peritoneal dialysis. HSP-72 expression in rat mesothelial cells harvested by trypsin peritoneal washout after a 4-hour dwell with either standard PDF (PDF) or PDF with added L-glutamine (GLN-PDF) was investigated. Addition of L-glutamine resulted in enhanced HSP-72 expression. Mesothelial cell detachment (FIG. 5) and peritoneal protein loss (FIG. 6) are shown as box (25th and 75th), whiskers (10th and 90th percentile) and median plots. L-glutamine addition to PDF was associated with significantly lower mesothelial cellular (MC) counts and decreased protein loss into the dialysate effluate. Data are obtained in 6 rats in each group in 3 independent experiments.

Material and Methods

In-Vitro Model of PD (Adapted from Reference No. 5)

Immortalized human mesothelial cells (Met5A, ATCC CRL-9444) were cultured in M199/MCDB 105 medium (1:1) supplemented with 100 units/ml penicillin, 100 μg/ml streptomycin and 10% FCS. Cultures were kept in 75 cm$^2$ tissue culture flasks (Falcon, Becton Dickinson, Oxnard, Calif.) at 37° C. in 5% $CO_2$ and passaged by regular trypsinization. Medium was changed every two to three days. Confluence was reached on average after 6 to 7 days.

Confluent cultures were then exposed for 120 minutes to standard glucose-monomer and acidic lactate-based PDF (Fresenius 2, Bad Homburg, Germany), containing 1.5% anhydrous dextrose at pH 5.5, with or without addition of cytoprotective compound (glutamine at 4 to 20 mM) and allowed to recover in regular growth medium for 16 hours. Control cultures were kept in regular culture media at 37° C. and underwent "sham media changes", i.e.: exposure to PDF was paralleled by exposure to control medium.

Viability of cells was assessed by lactate dehydrogenase (LDH) analyses. Fifty μl aliquots of supernatants were removed after the described experimental setup and kept on 4° C. until analyzed within 48 hours. Measurements were performed in duplicates with Sigma TOX-7 LDH Kit according to the manufacturer instructions. LDH efflux was calculated as percentage of LDH values measured in each negative control experiment. Induction of HSP was assessed in parallel cultures as described below.

In-Vivo Acute Rat Model of PD (Adapted from Reference No. 9):

The studies were carried out on adult male inbred Sprague Dawley rats (average weight 310 g). After introduction of anaesthesia (ketamine 100 mg/kg and 5 mg/kg xylazine, intramusculary) the animals were placed on a heated small animal operating table. A sterile catheter was inserted into the peritoneal cavity through a small abdominal midline incision and 35 ml of test fluid (PDF with or without addition of L-glutamine at 4-10 mM) were slowly infused in 45-60 secs. The animal was gently moved, a small volume of peritoneal fluid aspirated, the catheter withdrawn and the abdomen sutured. Animals awoke within 20 minutes after the procedure and had free access to food and tap water. At 4 hours after the intraperitoneal injection animals were again anaesthetized, another small volume of peritoneal fluid was aspirated and animals were sacrificed by cardial puncture and exsanguinations. Thereafter, the abdomen was opened by a midline incision and the complete intraperitoneal fluid gently collected. The volumes of the collected fluids were recorded, and total cell count and differential counts at the two time pints (0 and 4 hours) were assessed by hand count after giemsa staining and by machine count by a coulter counter. Total number of detached mesothelial cells was then computed for each rat. In selected animals, mesothelial cells lining the peritoneal cavity were harvested following the 4 hour dwell by peritoneal washout with 20 mL phosphate-buffered saline (PBS) containing 0.1% trypsin and 0.1% EDTA for 20 minutes.

For testing the barrier function of the peritoneal membrane, creatinine, glucose and total protein were measured in dialysate (D) samples and creatinine in plasma (P) at the end of the protocol. D/P ratios for creatinine and D/D0 ratios for glucose were computed. Peritoneal loss of protein was calculated as final dialysate concentration×final volume. All animals received humane care in compliance with the principles of laboratory animal care as prepared by the National Academy of Sciences and published by the National Institutes of Health.

HSP-72 Detection, and Statistics:

Western blotting: Protein content of mesothelial cell harvests was determined by Bradford assay (BioRad) and equal amounts of protein samples (5 μg/lane) were separated by standard SDS-PAGE using a Pharmacia Multiphore II unit. Size-fractionated proteins were transferred to PVDF membranes by semi-dry transfer in a Pharmacia Multiphore II Novablot unit. Membranes were blocked in 5% dry milk in TBS-Tween (10 mM Tris, 150 mM NaCl, 0.05% Tween 20, pH 8.0). Membranes were incubated with the HSP-72 antibody (SPA 810, Stressgen, B.C., Canada). Detection was accomplished by incubation with secondary, peroxidase-coupled antibodies (Sigma, USA) and enhanced chemiluminescence (ECL) using ECL Western blotting analysis system and protocols (Renaissance, NEN-Life Science Products, Boston, Mass., USA). Densitometry was performed with image analysis software (Molecular Analyst software, Bio-Rad, USA). Differential expression of HSP-72 was derived from the ratio of specific signals in the linear range of the protein/signal intensity relationship, normalized to an internal standard, and compared between parallel experiments.

Statistical analysis: Effects of treatments (+/−PDF exposure, +/−addition of cytoprotective additive (L-glutamine) were compared by multifactorial ANOVA in the in-vitro experiments. In the in-vivo experiments, effects of PDF exposure with versus without Glutamine addition were compared using the Mann-Whitney U test (Statview IV, Abacus, USA). Differences were considered to be significant given a $p<0.05$. The data are expressed as means+/−S.D.

Results

Cytoprotective Effect of L-Glutamine

The in-vitro experiments demonstrate HSP-mediated cytoprotection in mesothelial cells following addition of L-glutamine to the PDF.

FIGS. 1 and 2 demonstrate the effects of exposure to increasing doses of L-glutamine on cultured human mesothelial cells under control conditions. Addition of L-glutamine up to 20 mM resulted in unchanged viability, levels of 8 and 10 mM were associated with increased HSP-72 expression.

Effects of L-glutamine during standard PDF exposure on cultured human mesothelial cells are shown in FIGS. 3 and 4. Addition of L-glutamine to the PDF resulted in preserved viability and increased HSP-72 expression. LDH release increased from 100+/−3% under control conditions to 226+/−29% during exposure to PDF without cytoprotective agent versus 91+/−7 to 190+/−19% during exposure to PDF with added L-glutamine (FIG. 3). Multifactorial ANOVA demonstrated that effects of PDF exposure and effects of L-glutamine addition were both significant (p=0.0001 and p=0.001). These effects were interdependent, i.e. the (cytoprotective) effects of L-glutamine were significantly higher during (cytotoxic) PDF exposure (p=0.037).

HSP-72 expression increased from 100+/−43% under control conditions to 423+/−661% during exposure to PDF without cytoprotective agent versus 234+/−221 to 1895+/−1928 during exposure to PDF with added L-glutamine (FIG. 4). Again, multifactorial ANOVA demonstrated that effects of PDF exposure and effects of L-glutamine addition were both significant (p=0.003 and p=0.023). In addition, these effects were interdependent, i.e. the (HSP co-inducing) effects of L-glutamine were significantly higher during PDF exposure (p=0.011).

To confirm the biological role of pharmaceutical HSP-mediated cytoprotection in PD, the effects of enhancing HSP-72 expression by L-glutamine supplemented PDF on mesothelial cell detachment from their peritoneal monolayer in the rat model of PD were assessed. As shown in FIGS. 5 and 6, use of this cytoprotective PDF resulted in overexpression of HSP-72, and significantly reduced mesothelial cell detachment following in-vivo PDF exposure during a 4 hr dwell (93+/−39 cells vs 38+/−38 cells, p=0.044; FIG. 5). L-glutamine addition to PDF was also associated with decreased protein loss into the dialysate effluate (75+/−7 mg vs 65+/−4 mg, p=0.045; FIG. 6). There were no effects of L-glutamine supplementation on net ultrafiltration (6.8+/−1.1 ml vs 5.4+/−2.7 ml), D/P creatinine (0.414+/−0.08 vs 0.375+/−0.11) or D/Do glucose (0.473+/−0.02 vs 0.469+/−0.04).

According to the above examples, in an in-vitro model of PD, addition of L-glutamine resulted in marked HSP overexpression and improved mesothelial cell survival during PDF exposure.

These in-vitro findings therefore link HSP expression and cellular outcome in mesothelial cells, and clearly support the concept that a pharmacologic additive can induce HSP-mediated cytoprotection against PDF exposure.

In the final part of this study, HSP expression in the rat model of PD was manipulated by adding the HSP co-inducer L-glutamine to PDF. As expected from the in-vitro results, L-glutamine supplementation enhanced HSP expression in mesothelial cells during in-vivo exposure. Consistent with the concept of HSP-mediated cytoprotection, L-glutamine addition to PDF also resulted in a lower number of detached mesothelial cells. In good agreement with stabilization of the peritoneal mesothelial monolayer, evidence for an attenuated barrier dysfunction was found, as demonstrated by a lower protein content in the PD effluent of the treated rats. The in-vivo experiments thus extend the previous findings following heat-pretreatment to a more feasible pharmacological intervention model (9).

Links between increased HSP expression and improved outcome are also described in animal survival models of sepsis and hyperthermia following glutamine supplementation (17). In a small human randomized controlled trial in ICU patients, there was also a significant correlation between increases in serum HSP-70 and decrease in length of ICU stay following glutamine supplementation during parenteral nutrition (19). Finally, patients with critical disease have been shown to frequently suffer from glutamine depletion, supporting the potential for glutamine supplementation in that population (13).

Cytoprotective Effect of a Dipeptide Capable of Releasing L-glutamine in Free Form.

The acute recovery experimental setting as described for glutamine as a proof of principle for the cytoprotective PDF, is best representative for the early toxic effects of PDF, mainly due to low pH and lactate as major culprits. Alternate models such as a longterm exposure model to unused PDF diluted 1:1 with normal culture medium are better accepted tools to assess effects of cellular processes that occur in the peritoneum upon more extended exposure to PDF, as occurs in clinical PD.

Therefore, L-alanyl-L-glutamine is tested for its potential to confer cytoprotective effects by exposing confluent cultures for 24 hours to conventional acidic lactate-based PDF, containing 1.5% anhydrous dextrose, diluted 1:1 with M199 medium containing 10% FCS without or with addition of L-alanyl-L-glutamine at a concentration of 0.5 and 10.0 g/L ("low and high dose"). Additional control cultures are kept in pure regular culture media at 37° C. for the same time. At the end of the study, cell viability and protein expression are assessed in parallel cultures to identify the cytoprotective PDF.

The in-vitro experiments demonstrate HSP-mediated cytoprotection in mesothelial cells following exposure to PDF with addition of L-alanyl-L-glutamine similar to what had been demonstrated for glutamine. The cytoprotective PDF containing L-alanyl-L-glutamine results in preserved viability assessed by LDH release and increased HSP-72 expression when compared to standard PDF exposure.

Taken together, the concordant effects of the novel PDFs according to the present invention on HSP expression and cellular outcome clearly support the concept of HSP mediated cytoprotection in PD. More specifically, a high potential for L-glutamine as an additive to PDF to optimize mesothelial cellular responses to pathophysiological stress upon in-vitro and in-vivo PDF exposure was delineated. Such HSP mediated cytoprotection upon glutamine addition to PDF will likely have biological relevance, as it was associated with decreased mesothelial cell detachment and lower peritoneal protein loss following acute PDF exposure. Given the deranged glutamine metabolism in patients with chronic renal failure, glutamine, and dipeptides capable of releasing glutamine in free form represent an extremely attractive candidate as "cytoprotective additive" to PDF (15).

REFERENCES

1. Arbeiter K, Bidmon B, Endemann M, et al (2001) Peritoneal dialysate fluid composition determines heat shock protein expression patterns in human mesothelial cells. Kidney Int 60:1930-1937
2. Arbeiter K, Bidmon B, Endemann M, et al (2003) Induction of mesothelial HSP-72 in mesothelial cells exposed to peritoneal dialysis fluid. Pent Dial Int 23:499-501
3. Aufricht C (2005) Heat-shock protein 70: Molecular supertool? Pediatr Nephrol 20:707-13
4. Aufricht C, Endemann M, Bidmon B, Arbeiter K, et al (2001) Peritoneal dialysis fluids induce the stress response in human mesothelial cells. Perit Dial Int 21:85-88
5. Bidmon B, Endemann M, Arbeiter K, Ruffingshofer D et al (2004) Overexpression of HSP-72 confers cytoprotection in experimental peritoneal dialysis. Kidney Int 66:2300-2307
6. Davies S J, Phillips L, Griffiths A M, et al (1998) What really happens to people on longterm peritoneal dialysis? Kidney Int 54: 2207-17
7. Devuyst O, Topley N, Williams J D (2002) Morphological and functional changes in the dialysed peritoneal cavity: impact of more biocompatible solutions. Nephrol Dial Transplant. 17 S3:12-5
8. Eliasen M M, Brabec M, Gerner C, et al (2006) Reduced stress tolerance of glutamine-deprived human monocytic cells is associated with selective down-regulation of Hsp70 by decreased mRNA stability. J Mol Med. 84:147-58.
9. Endemann M, Bergmeister H, Boehm M, et al (2007) Evidence for HSP-mediated cytoskeletal stabilization in mesothelial cells during acute experimental peritoneal dialysis. American J Physiol Renal Physiol. 292 January Issue
10. Jorres A, Topley N, Gahl G M (1992) Biocompatibility of peritoneal dialysis fluids. Int J Artif Organs 15:79-83
11. Lee B S, Chen J, Angelidis C, et al (1995) Pharmacological modulation of heat shock factor 1 by antiinflammatory drugs results in protection against stress-induced cellular damage. Proc Natl Acad Sci USA. 92:7207-11.
12. Morrison A L, Dinges M, Singleton K D, et al (2006) Glutamine's protection against cellular injury is dependent on heat shock factor-1. Am J Physiol Cell Physiol. 290:C1625-32.

13. Novak F, Heyland D K, Avenell A, et al (2002) Glutamine supplementation in serious illness: a systematic review of the evidence. Crit Care Med. 30:2022-9.
14. Oehler R, Roth E (2003) Regulative capacity of glutamine. Curr Opin Clin Nutr Metab Care 6:277-82
15. Raj D S, Welbourne T, Dominic E A, et al (2005) Glutamine kinetics and protein turnover in end-stage renal disease. Am J Physiol Endocrinol Metab. 288:E37-46.
16. Ruffingshofer D, Endemann M, Arbeiter K, et al (2003) Induction of heat shock protein-72 in mesothelial cells exposed to peritoneal dialysis effluent. Petit Dial Int 23:74-77
17. Singleton K D, Wischmeyer P E (2006) Oral glutamine enhances heat shock protein expression and improves survival following hyperthermia. Shock. 25:295-9.
18. Wischmeyer P E (2002) Glutamine and heat shock protein expression. Nutrition. 18:225-8
19. Ziegler T R, Ogden L G, Singleton K D, et al (2005) Parenteral glutamine increases serum heat shock protein 70 in critically ill patients. Intensive Care Med. 31:1079-86.
20. Saeed Alhamdani et al. (2007) Antiglycation and antioxidant effect of carnosine against glucose degradation products in peritoneal mesothelial cells. Nephron Clin Pract 107:c26-34.
21. Breborowicz A, Witowski J, Polubinska A et al (2004) L-2-oxothiazolidine-4-carboxylic acid reduces in vitro cytotoxicity of glucose degradation products. Nephrol Dial Transplant. 19:3005-11
22. Inagi R, Miyata T, Ueda Y et al (2002) Efficient in vitro lowering of carbonyl stress by the glyoxalase system in conventional glucose peritoneal dialysis fluid. Kidney Int 62:679-87.
23. Fürst P (2001) New Developments in Glutamine Delivery, J Nutrition 131 (9 Suppl):2562S-8S

The invention claimed is:

1. A glucose-based peritoneal dialysis fluid comprising:
a peritoneal dialysis fluid comprising glucose; and
a dipeptide that is glutaminyl-glycine, glycinyl-glutamine, glutaminyl-alanine or alanyl-glutamine, or a mixture of two or more of said dipeptides, wherein the concentration of said dipeptide in the dialysis fluid is 2 mM to 25 mM,
wherein the glucose concentration in the dialysis fluid is 10 g/l to 45 g/l, and
wherein the glucose-based peritoneal dialysis fluid does not include glutamine in its monomeric form and wherein the glucose-based peritoneal dialysis peritoneal dialysis fluid only contains amino acids in dipeptide form.

2. The peritoneal dialysis fluid according to claim 1, wherein said dipeptide is at least one member selected from the group consisting of alanyl-glutamine and glutaminyl-alanine.

3. The peritoneal dialysis fluid according to claim 1, wherein said dialysis fluid comprises alanyl-glutamine.

4. The peritoneal dialysis fluid according to claim 1, wherein the peritoneal dialysis fluid is suitable for use in peritoneal dialysis in a patient.

5. The peritoneal dialysis fluid according to claim 1, wherein the glutamine is L-glutamine.

6. A glucose-based peritoneal dialysis fluid consisting essentially of:
a peritoneal dialysis fluid comprising glucose; and
a dipeptide that is glutaminyl-glycine, glycinyl-glutamine, glutamine-alanine or alanyl-glutamine, or a mixture of two or more of said dipeptides, wherein the concentration of said dipeptide in the dialysis fluid is 2 mM to 25 mM,
wherein the glucose concentration in the dialysis fluid is 10 g/l to 45 g/l and wherein the glucose-based peritoneal dialysis fluid only contains amino acids in dipeptide form.

7. The peritoneal dialysis fluid according to claim 6, wherein said dipeptide is at least one member selected from the group consisting of alanyl-glutamine and glutaminyl-alanine.

8. The peritoneal dialysis fluid according to claim 6, wherein said dialysis fluid comprises alanyl-glutamine.

9. The peritoneal dialysis fluid according to claim 6, wherein the peritoneal dialysis fluid is suitable for use in peritoneal dialysis in a patient.

10. The peritoneal dialysis fluid according to claim 6, wherein the glutamine is L-glutamine.

11. A method for preparing the glucose-based peritoneal dialysis fluid of claim 1 comprising admixing a dipeptide that is glutaminyl-glycine, glycinyl-glutamine, glutaminyl-alanine or alanyl-glutamine, or a mixture of two or more of said dipeptides, with a carbohydrate-based peritoneal dialysis fluid to provide a final concentration of said dipeptide of from 2 mM to 25 mM.

* * * * *